United States Patent
Sellberg et al.

(10) Patent No.: US 11,188,676 B2
(45) Date of Patent: Nov. 30, 2021

(54) HEALTHCARE MONITORING METHOD AND SYSTEM FOR SECURE COMMUNICATION OF PATIENT DATA

(71) Applicant: ADDI MEDICAL AB, Stockholm (SE)

(72) Inventors: Nina Sellberg, Stockholm (SE); Casper Wisnes, Saltsjö-Boo (SE); Fredrik Henriques, Stockholm (SE)

(73) Assignee: Addi Medical AB, Stockholm (SE)

( * ) Notice: Subject to any disclaimer, the term of this patent is extended or adjusted under 35 U.S.C. 154(b) by 460 days.

(21) Appl. No.: 16/330,500

(22) PCT Filed: Sep. 5, 2017

(86) PCT No.: PCT/EP2017/072237
§ 371 (c)(1),
(2) Date: Mar. 5, 2019

(87) PCT Pub. No.: WO2018/046495
PCT Pub. Date: Mar. 15, 2018

(65) Prior Publication Data
US 2019/0188415 A1    Jun. 20, 2019

Related U.S. Application Data

(60) Provisional application No. 62/383,716, filed on Sep. 6, 2016.

(51) Int. Cl.
*G06F 21/62* (2013.01)
*G16H 10/60* (2018.01)
(Continued)

(52) U.S. Cl.
CPC ...... *G06F 21/6245* (2013.01); *G06F 21/6254* (2013.01); *G16H 10/60* (2018.01);
(Continued)

(58) Field of Classification Search
CPC .. G06F 21/6245; G06F 21/6254; G06F 21/62; H04L 9/3226; H04L 9/0819;
(Continued)

(56) References Cited

U.S. PATENT DOCUMENTS

2005/0165623 A1* 7/2005 Landi ............... G16H 10/60
705/2
2008/0304663 A1* 12/2008 Canard ............ G06F 21/6254
380/45

FOREIGN PATENT DOCUMENTS

WO      2012015645 A2    2/2012

OTHER PUBLICATIONS

Swedish Search Report for corresponding Swedish Application No. 1950412-5 dated Mar. 18, 2020.

* cited by examiner

*Primary Examiner* — Pei Yong Weng
(74) *Attorney, Agent, or Firm* — Renner, Otto, Boisselle & Sklar, LLP

(57) ABSTRACT

There is provided a method in a healthcare monitoring system for anonymous communication of patient data associated with a patient from an electronic user device, using a patient application implemented in the electronic user device, to a host server, using a host application implemented in the host server, via a wireless network, and identification of the patient associated with the patient data after the patient data is received in the host server. There is further provided a corresponding system, computer program and non-volatile data carrier containing the computer program.

12 Claims, 5 Drawing Sheets

(51) Int. Cl.
*H04L 9/32* (2006.01)
*H04L 9/08* (2006.01)

(52) U.S. Cl.
CPC .......... *H04L 9/0819* (2013.01); *H04L 9/3226* (2013.01); *H04L 2209/88* (2013.01)

(58) Field of Classification Search
CPC ....... H04L 2209/88; H04L 9/08; G16H 10/60; G16H 10/00
See application file for complete search history.

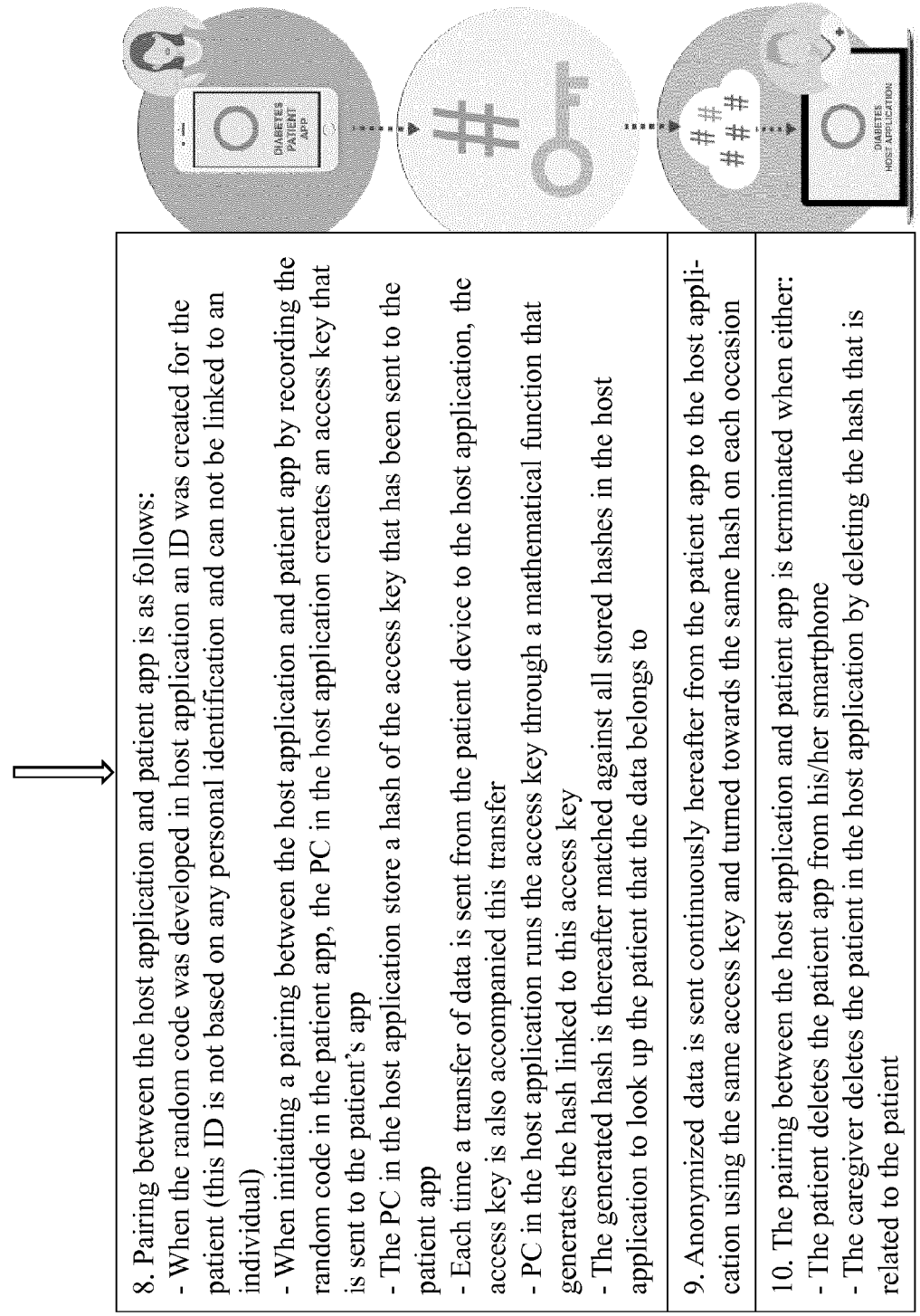

8. Pairing between the host application and patient app is as follows:
- When the random code was developed in host application an ID was created for the patient (this ID is not based on any personal identification and can not be linked to an individual)
- When initiating a pairing between the host application and patient app by recording the random code in the patient app, the PC in the host application creates an access key that is sent to the patient's app
- The PC in the host application store a hash of the access key that has been sent to the patient app
- Each time a transfer of data is sent from the patient device to the host application, the access key is also accompanied this transfer
- PC in the host application runs the access key through a mathematical function that generates the hash linked to this access key
- The generated hash is thereafter matched against all stored hashes in the host application to look up the patient that the data belongs to 9. Anonymized data is sent continuously hereafter from the patient app to the host application using the same access key and turned towards the same hash on each occasion 10. The pairing between the host application and patient app is terminated when either:
- The patient deletes the patient app from his/her smartphone
- The caregiver deletes the patient in the host application by deleting the hash that is related to the patient FIG. 4
(continuation)

HEALTHCARE MONITORING METHOD AND SYSTEM FOR SECURE COMMUNICATION OF PATIENT DATA

RELATED APPLICATIONS

This application is a national phase entry of International Application No. PCT/EP2017/072237 filed on Sep. 5, 2017 and published in the English language, which claims the benefit of U.S. Provisional Application No. 62/383,716 filed Sep. 6, 2016, both of which are hereby incorporated by reference.

TECHNICAL FIELD

The present invention relates generally to solutions for enabling secure communication of patient data.

More particularly, the invention relates to a method for enabling secure communication of patient data according to the preamble of claim 1, and corresponding system. The invention also relates to a computer program and a non-volatile data carrier.

BACKGROUND

Healthcare is used as an example of an owner of a host application in the text below. The owner of the host application could be any party or organization that could have an interested in an individual's/patient's registered health data. The health data is represented as quantitative data such as number of steps, weight, electrocardiography measures, spirometer measures, blood pressure, degree of patient's perceptive of pain etc. or qualitative data which is the individual's perception written in free text format.

The party and/or organisation having interest in the individual's registered quantitative or qualitative data described could be public or private healthcare, academic research projects, industry research projects, public/private registries, qualitative registries, bio banks, health authorities etc. The data might also be retrieved on a consent basis for follow-up of the sale of consumer goods for functionality or quality checks and for customer satisfaction screening or for direct marketing purposes. Another party having interest in the individual's registered quantitative or qualitative data could be the pharmaceutical industry.

When we refer to the patient's "app", or "patient application", this includes the Patient Connector (PC) and also the patient's unit/device/client that the app is implemented in. When we refer to the caregiver's "host application" this includes the Patient Connector ("PC") and also the caregiver's server/unit/system.

Transfer of data means that information is sent via a message between the app in the patient's device and the host application on healthcare's server.

A Software Development Kit ("SDK") is a component/set of software development tools that allows the creation of applications for a certain software package, software framework, patient application, electronic health record, research system or other applications and systems.

SUMMARY

Secure communication by connecting a host application with an app in a patient device (also referred to as a patient application), holding patient registered or patient generated information. The host application and the app in the patient device has been paired through an authorization process done using strong authorization, either during a meeting in person or using the host application and/or the app in the patient application. The PC is distributed as a software development kit (SDK) that is imported into any host application and any patient app. The PC pairs the host application with the patient app in a secure and accurate way. The PC provides transferring of anonymous patient information between the app in the patient device and the host application.

According to an aspect there is provided a method in a healthcare monitoring system for anonymous communication of patient data associated with a patient from an electronic user device, using a patient application implemented in the electronic user device, to a host server, using a host application implemented in the host server, via a wireless network, and identification of the patient associated with the patient data after the patient data is received in the host server, the method comprising:

pairing the patient application 110 and the host application 130, wherein the pairing comprises generating a unique access key K for the patient P, using the host application 130, wherein the unique access key K is unrelated to any information identifying the patient P, wherein the unique access key K comprises a first part K_1 and a second part K_2; storing the second part K_2 of the unique access key K in a memory 160 accessible by the host application 130, wherein the second part K_2 is stored in association with information identifying the patient P; sending the first part K_1 of the unique access key K from the host application 130 to the patient application 110; storing the first part K_1 of the unique access key K in a memory 150 accessible by the patient application 110;

receiving in the patient application 110 patient data D, from at least one patient data registering device 170;

in response to receiving patient data D in the patient application 110, sending the received patient data D and the first part of the access key K_1 to the host application 130;

receiving in the host application 130 the patient data D and the first part of the access key K_1; and identifying the patient P associated with the received patient data D, based on the second part K_2 of the access key K.

In some embodiments, the method further comprises, prior to pairing the patient application 110 and the host application 130: authenticating a caregiver as an authorized user of the host application 130, using strong authentication; and authenticating a patient as an authorized user of the patient application 130, using strong authentication. Authenticating the caregiver may be performed using the host application 130. Authenticating the patient P may be performed using the patient application 110.

In one or more embodiments, the method may further comprise storing the received patient data D in the memory 150 accessible to the patient application 110;

In one or more embodiments, identifying the patient P associated with the received patient data D, based on the second part K_2 of the access key K, comprises: generating a second part K_2 of the access key K, based on the received first part K_1 of the access key K; comparing the generated second part K_2 of the access key K to one or more second parts of access keys stored in the memory 160 accessible to the host application 130 to find a matching second part, wherein the stored one or more second parts of access keys have been generated during pairing of the host application 150 with one or more patient applications 110; and if a matching second part of an access key is found, identifying the patient P as the patient associated with the matching second part stored in the memory 160.

In one or more embodiments, the first part K_1 of the unique access key K is the original key and second part K_2 of the unique access key K is a hash or thumbprint of the original key.

In one or more embodiments, generating a unique access key K for the patient P comprises: generating, using the host application 130, a randomized numeric code C that is unrelated to any information identifying the patient P; receiving, in the patient application 110, the randomized numeric code C; sending a message in the form of a control signal S1 from the patient application 110 to the host application 130 in response to receiving the unique access key K; receiving, in the host application 130, the control signal S1; and generating, in the host application 130, the unique access key K in response to receiving the control signal S1.

According to another aspect there is provided a healthcare monitoring system 100 for anonymous communication of patient data D associated with a patient P from an electronic user device 120 to a host server 140, via a wireless network 180, and identification of the patient P associated with the patient data D after the patient data D is received in the host server 140, wherein the electronic user device 120 comprises a patient application 110; and the host server 140 comprises a host application 130; and wherein the patient application 110 is configured to communicate with the host application 130 via the wireless network 180. The system 100 further comprises a memory 150 accessible by the patient application 110 and a memory 160 accessible by the host application 130. The system 100 is configured to pair the patient application 110 and the host application 130, by:

the host application being configured to: generate a unique access key K for the patient P, wherein the unique access key K is unrelated to any information identifying the patient P, wherein the unique access key K comprises a first part K_1 and a second part K_2; store the second part K_2 of the unique access key K in the memory 160 accessible by the host application 130, wherein the second part K_2 is stored in association with information identifying the patient P; and send the first part K_1 of the unique access key K to the patient application 110;

the patient application 110 being configured to: receive first part K1 of the unique access key K from the host application 130; store the received first part K_1 of the unique access key K in the memory 150 accessible by the patient application 110; receive patient data D, from at least one patient data registering device 170; and in response to receiving patient data D in the patient application 110, send the received patient data D and the first part of the access key K_1 to the host application 130; and the host application 130 further being configured to: receive patient data D and the first part of the access key K_1 from the patient application 100; and identify the patient P associated with the received patient data D, based on the received second part K_2 of the access key K.

In some embodiments, the host application 130 is configured to authenticate a caregiver as an authorized user of the host application 130, using strong authentication, prior to the pairing of the patient application 110 and the host application 130.

In some embodiments, the patient application 110 is configured to authenticate a patient P as an authorized user of the patient application 110, using strong authentication, prior to the pairing of the patient application 110 and the host application 130.

In some embodiments, the host application 130 is further configured to identify the patient P associated with the received patient data D, based on the second part K_2 of the access key K, by: generating a second part K_2 of the access key K, based on the received first part K_1 of the access key K; comparing the generated second part K_2 of the access key K to one or more second parts of access keys stored in the memory 160 accessible to the host application 130 to find a matching second part, wherein the stored one or more second parts of access keys have been generated during pairing of the host application 150 with one or more patient applications 110; and if a matching second part of an access key is found, identifying the patient P as the patient associated with the matching second part stored in the memory 160.

In some embodiments, in order to generate a unique access key K for the patient P: the host application 130 is configured to generate a randomized numeric code C that is unrelated to any information identifying the patient P; the patient application 110 is configured to receive the randomized numeric code C from the host application 130; and send a message in the form of a control signal S1 to the host application 130 in response to receiving the unique access key K; and the host application 130 is configured to receive the control signal S1 from the patient application 110; and generate the unique access key K in response to receiving the control signal S1.

According to yet another aspect there is provided a computer program loadable into a non-volatile data carrier communicatively connected to a processing unit, the computer program comprising software for executing the method according any of the embodiments presented herein when the program is run on the processing unit.

According to still another aspect there is provided a non-volatile data carrier containing the computer program described above.

DESCRIPTION OF THE FIGURES

The invention is now to be explained more closely by means of preferred embodiments, which are disclosed as examples, and with reference to the attached drawings.

DESCRIPTION OF THE INVENTION

Figure 1:
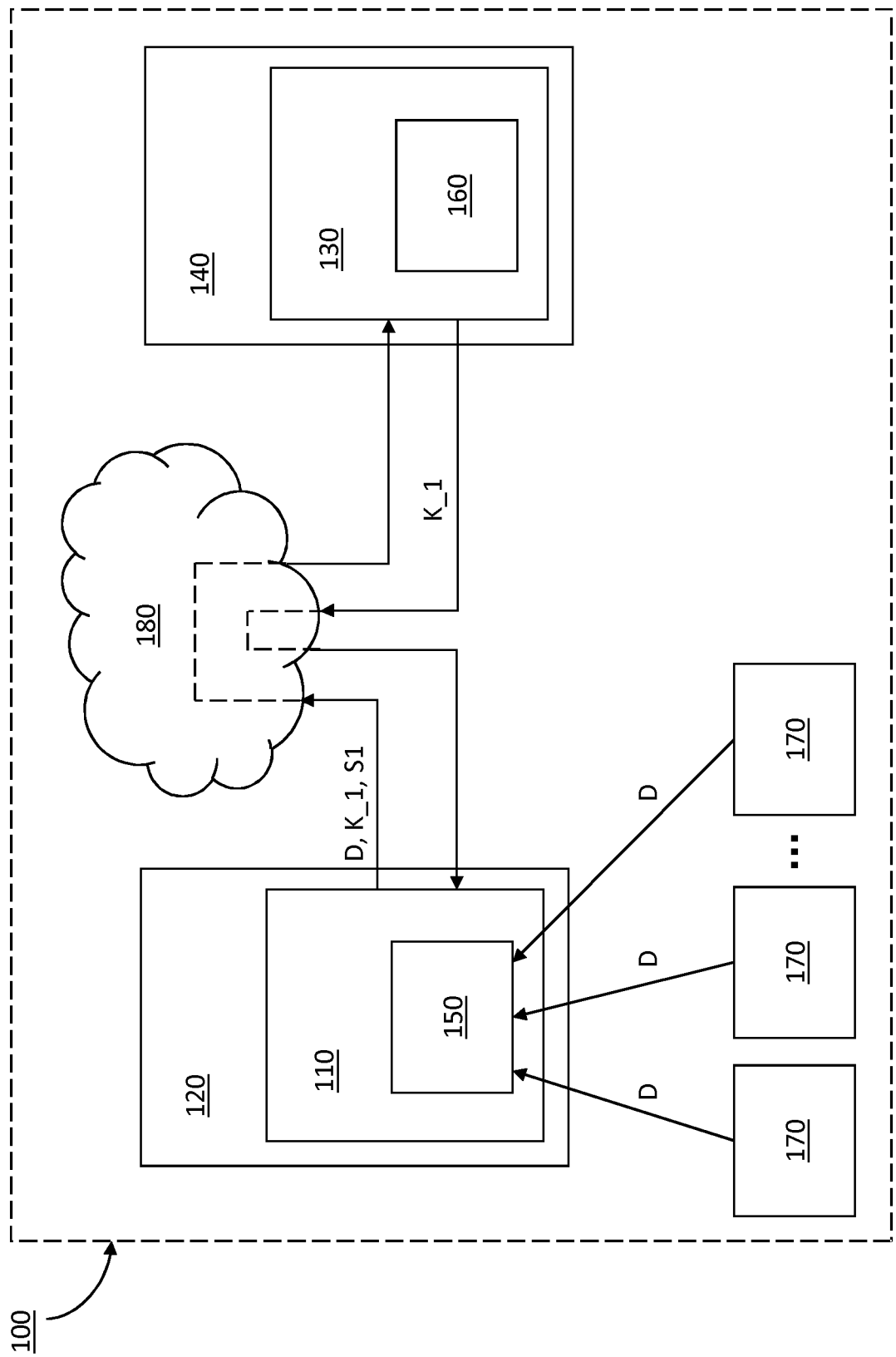
FIG. 1 shows an overview of a system according to one or more embodiments of the invention.

The subject invention provides secure communication by transferring information that does not include personal or individual identification information so as to keep the identity of the information provider(s) confidential during the transfer of information. The patient's app and the host application will pair through the PC by utilizing a randomized generated code that is unique for the subject patient. The randomized code is transferred into an ID/access key in the patient app that is known to the host application. The ID/access key is matched with a stored hash in the host application to identify the information provider.

In other words, embodiments presented herein enable secure communication of confidential and sensitive patient data, even via open, wireless networks such as the Internet, because the patient data is completely anonymous during the transfer from the patient application (patient's app) to the host application. This is essential because there are strict regulations controlling handling of sensitive patient data that need to be fulfilled. For instance, embodiments presented herein aim at fulfilling the EU General Data Protection Regulation (GDPR).

In addition to this, embodiments presented herein further enable the host application, e.g. a healthcare provider/care giver to accurately associate the patient data with the correct patient's identity after the patient data has been received from the patient application. This is also essential, as the medical data sent by the patient is useless to the healthcare provider/caregiver if it cannot be established without a doubt with which patient the received patient data is associated. Not to mention that if it cannot be established without a doubt with which patient the received patient data is associated, patient security would be jeopardized due to risk of providing the wrong treatment to the wrong patient, or not providing treatment to a patient in need of it, e.g.

The invention provides a solution to the technical problem of transferring securely sensitive information over the internet or through other information networks. The subject invention realizes the solution by providing means and methods of sending such information unidentified and without personal identity information and pairing the unidentified information at the reception by the host with the identity information in the ID/access key. There was prior to the invention no solution to the challenge of sending unidentified patient data over the Internet and still be able to connect securely patient registered data in a patient app to a host application, e.g. a health care decision support system, electronic healthcare record, or a research institution's information system or any other health or biotech related registry. Within the context of the present disclosure, patient registered data may be replaced with, or complemented by, patient generated data, without any modifications of the method and system embodiments being necessary. Current host systems are unable to tell with acceptable certainty what information belongs to which patient without accommodating patient identity information during the transfer of information. For applications where patients are transferring patient registered data to a health care provider for diagnosing or health care follow-up there is a need of un-identification, security and accuracy mechanisms when transferring data. The suggested invention resolves this problem by pairing the patient app and the host application during a meeting in person between the patient and for instance a medical professional from healthcare. Alternatively, the meeting could be with a person conducting a pharmaceutical research project. In relation to this meeting the patient has securely identified herself at the registration desk at a department in a hospital and the medical professional has identified herself, with so called strong authentication, when logging into the host application. The procedures of identification/authentication meet required degrees of security and accuracy.

As an alternative, also the patient identifies herself, using so called strong authentication, when logging into the patient application or using another system provided by the medical professional from healthcare. Also in this case, the procedures of identification/authentication meet required degrees of security and accuracy.

Furthermore, in connection with performing the pairing of applications, the patient knowingly consents to the host application, and in turn the host (medical staff, caregiver or other actor as described herein), having access to the patient data that is anonymously communicated from the patient application to the host application, and further having access to information uniquely identifying the patient associated with the patient data. According to embodiments described herein in connection with the figures, each time patient data is to be sent from the patient application and also each time identification is to be performed in the host application, a check is performed to determine whether a pairing exists between the host application and the patient application. In other words, the patient consent is checked every time. If the patient should for some reason no longer consent to sharing her patient data and identification data, the patient may delete the patient application from her smartphone or other user device where the patient application has been installed. Thereby, when the next check is performed, in step 240 or 280 in connection with FIG. 2, no pairing is found and the method ends. Thereby, a required degree of security is obtained to e.g. fulfill GDPR and other relevant legal regulations.

In FIG. 1, embodiments of a healthcare monitoring system 100 for anonymous communication of patient data D, associated with a patient P, from an electronic user device to a host server, via a wireless network, and identification of the patient P associated with the patient data D after the patient data D is received in the host server, are shown.

According to one or more embodiments, the healthcare monitoring system 100 comprises an electronic user device 120, which comprises a patient application 110; and a host server 140, which comprises a host application 130. The patient application 110 is configured to communicate with the host application 130 via a wireless network 180. The system 100 further comprises a memory 150 accessible by the patient application 110 and a memory 160 accessible by the host application 130. In one or more embodiment, the system 100 is configured to pair the patient application 110 and the host application 130. This is achieved by the host application being configured to i) generate a unique access key K for the patient P, wherein the unique access key K is unrelated to any information identifying the patient P, wherein the unique access key K comprises a first part K_1 and a second part K_2; ii) store the second part K_2 of the unique access key K in the memory 160 accessible by the host application 130, wherein the second part K_2 is stored in association with information identifying the patient P; and iii) send the first part K_1 of the unique access key K to the patient application 110; whereby the patient application 110 is configured to i) receive first part K_1 of the unique access key K from the host application 130; ii) store the received first part K_1 of the unique access key K in the memory 150 accessible by the patient application 110; iii) receive patient data D, from at least one patient data registering device 170; and iv) in response to receiving patient data D in the patient application 110, send the received patient data D and the first part of the access key K_1 to the host application 130. The host application 130 is further configured to: i) receive patient data D and the first part of the access key K_1 from the patient application 100; and ii) identify the patient P associated with the received patient data D, based on the received second part K_2 of the access key K. Thereby, the patient data D is anonymous and secure when it is sent via the wireless network, but is uniquely identified as being associated with the patient P after it is received in the host application.

The host application 130 may be configured to authenticate a caregiver as an authorized user of the host application 130, using strong authentication, prior to the pairing of the patient application 110 and the host application 130.

In some embodiments, the patient application 110 is configured to authenticate a patient P as an authorized user of the patient application 110, using strong authentication, prior to the pairing of the patient application 110 and the host application 130.

In some embodiments, the host application 130 is configured to identify the patient P associated with the received patient data D, based on the second part K_2 of the access key K, by: i) generating a second part K_2 of the access key K, based on the received first part K_1 of the access key K; ii) comparing the generated second part K_2 of the access key K to one or more second parts of access keys stored in the memory 160 accessible to the host application 130 to find a matching second part, wherein the stored one or more second parts of access keys have been generated during pairing of the host application 150 with one or more patient applications 110; and iii) if a matching second part of an access key is found, identifying the patient P as the patient associated with the matching second part stored in the memory 160.

In one or more embodiments, generating a unique access key K for the patient P is enabled by the host application 130 being configured to generate a randomized numeric code C that is unrelated to any information identifying the patient P; the patient application 110 being configured to receive the randomized numeric code C from the host application 130 and send a message in the form of a control signal S1 to the host application 130 in response to receiving the unique access key K; and the host application 130 being configured to receive the control signal S1 from the patient application 110 and generate the unique access key K in response to receiving the control signal S1.

The healthcare monitoring system 100 comprises or is connected to a memory 150 accessible to the patient application 110. The healthcare monitoring system 100 further comprises or is connected to a memory 160 accessible to the host application 130. In FIG. 1, memory 150 is illustrated as being part of the patient application 110 and memory 160 is illustrated as being part of the host application 130. However, the memory 150 may be integrated in, connected to, or communicatively coupled to the patient application 110, and the memory 160 may be integrated in, connected to, or communicatively coupled to the host application 130.

Figure 2:
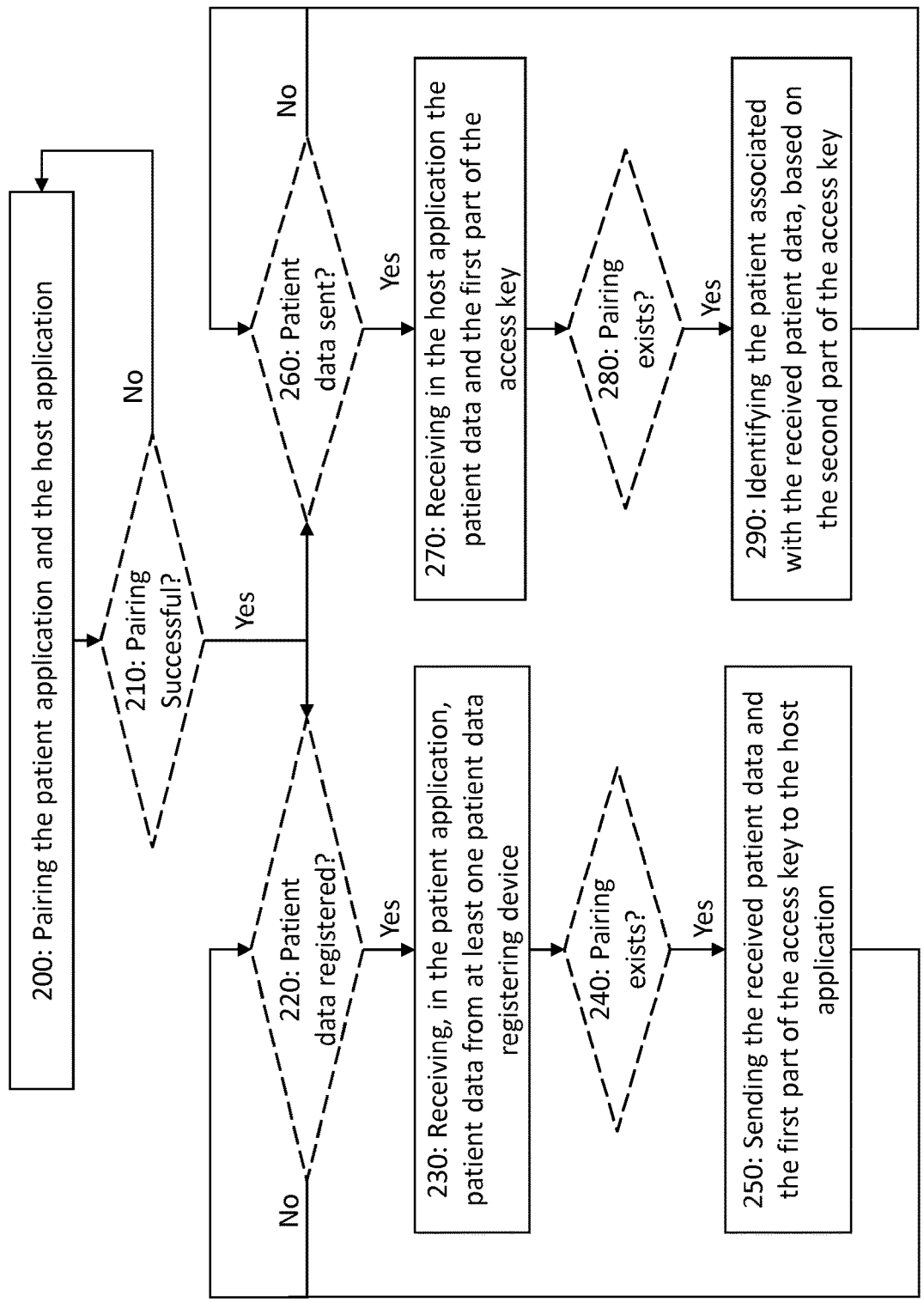
FIG. 2 shows a flow diagram illustrating a process for secure communication of digital information, comprising steps according to one or more embodiments of the proposed method.

FIG. 2 shows a flow diagram illustrating one or more embodiments of a method/process in a healthcare monitoring system 100 for anonymous communication of patient data D, associated with a patient P, from an electronic user device 120, using a patient application 110 implemented in the electronic user device 120, to a host server 140, using a host application 130 implemented in the host server 140, via a wireless network 180, and further for identification of the patient P, associated with the patient data D, after the patient data D is received in the host server 140.

According to one or more embodiments illustrated by FIG. 2, the method comprises:

In step 200: Pairing the patient application 110 and the host application 130.

Of course, a host application 130 can be paired with one or more patient applications 110, for receiving patient data from corresponding one or more patients.

In an optional step 210: Checking if the pairing in step 200 was successful.

According to embodiments wherein the method step 210 of checking whether the pairing in step 200 was successful is performed:
if the pairing was not successful, the method returns to step 200 to allow for another, optional, paring attempt; or
if the pairing was successful, the method continues according to step 220 and step 260, respectively.

Steps 220-250 below describe the method steps performed by the patient application 110, and steps 260-290 describe the method steps performed by the host application 130.

In one or more embodiments, the patient application 110 is configured to perform any or all of the method steps 220-250.

In one or more embodiments, the host application 130 is configured to perform any or all of the method steps 220-250.

In an optional step 220: Checking whether patient data D has been registered.

The patient data D may have been registered by at least one patient data registering device 170, wherein the at least one patient data registering device 170 may comprise a selection of the following: one or more sensors for blood pressure rate, heart rate, breath rate, ECG/EKG (electrocardiogram), respirations, blood oxygen levels, blood temperature, spirometer, or medtech equipment (ultra sound, patient monitor anesthesia, X-Ray mobile, oxygen concentrator, coagulometer, scale for adults, CT-scanner, one or more digital forms, or applications such as e.g. Health Kit or Google Fit.

According to embodiments wherein the method step 220 of checking whether patient data D has been registered is performed:
if no patient data D has been registered, the method returns to step 220; or
if patient data D has been registered, the method continues according to step 230.

In step 230: Receiving, in the patient application 110, patient data D from at least one patient data registering device 170.

Receiving patient data D may also be referred to as new relevant data being generated in the patient application 110.

In an optional step 240: Checking whether a pairing exists between the patient application 110 and the host application 130.

Reasons that a pairing may no longer exist are e.g. that: pairing between the host application 130 and patient application 110 has been terminated either by the patient P deleting the patient application 110 from her smartphone or other user device where the patient application 110 has been installed; the healthcare provider deleting the patient in the host application 130 by deleting the second part K_2 (e.g. the hash) of the unique access key K that is related to/associated with the patient identifying information; or due to an error.

According to embodiments wherein the method step 210 of checking whether a pairing exists between the patient application 110 and the host application 130:
if no pairing exists, the method ends and no further patient data D is communicated from the patient application 110 to the host application 130; or
if a pairing exists, the method continues according to step 250.

In step 250: Sending the received patient data D and the first part K_1 of the access key K to the host application 130.

Sending the received patient data D and the first part K_1 of the access key K to the host application 130 is done in response to receiving patient data D in the patient application 110.

Figure 4:
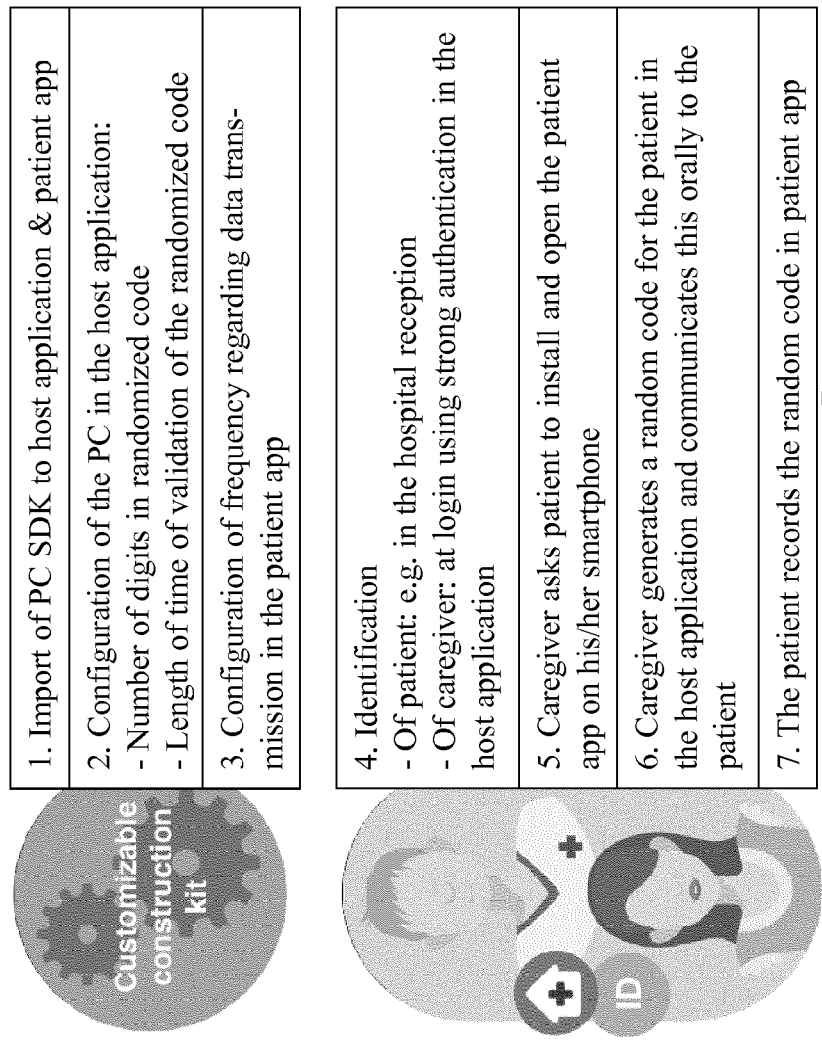
FIG. 4 shows a flow diagram illustrating a process for secure communication of digital information, comprising steps according to one or more embodiments of the proposed method.

As mentioned in connection with FIG. 4, information is hereafter securely and automatically transferred, according to the patient application 110 configuration, between the patient application 110 and the host application 130. According to different settings or configurations of the patient application 110, patient data D may be sent/transferred to the host application 130 continuously, at certain time intervals, only at certain times, e.g. only at night, or according to any other suitable rules/configuration depending on the circumstances.

In an optional step 260: Checking whether patient data D has been sent.

According to embodiments wherein the method step 260 of checking whether patient data D has been sent is performed:
- if patient data D has not been sent, the method repeats step 260; or
- if patient data D has been sent, the method continues according to step 270.

In step 270: Receiving in the host application 130 the patient data D and the first part K_1 of the access key K.

In step an optional step 280: Checking whether a pairing exists between the patient application 110 and the host application 130.

According to embodiments wherein the method step 280 of checking whether a pairing exists between the patient application 110 and the host application 130:
- if no pairing exists, the method ends; or
- if a pairing exists, the method continues according to step 290.

In step 290: Identifying the patient P associated with the received patient data D, based on the second part of the access key K.

In one or more embodiments, the pairing of step 200 comprises sub-steps 310-340, wherein:

In sub-step 310: Generating a unique access key K for the patient P, using the host application 130, wherein the unique access key K is in itself unrelated to any information identifying the patient P, wherein the unique access key K comprises a first part K_1 and a second part K_2.

Sub-step 310 of generating a unique access key K for the patient P may in turn comprise:
- generating, using the host application 130, a randomized numeric code C that is unrelated to any information identifying the patient P;
- receiving, in the patient application 110, the randomized numeric code C;
- sending a message in the form of a control signal S1 from the patient application 110 to the host application 130 in response to receiving the unique access key K;
- receiving, in the host application 130, the control signal S1; and
- generating, in the host application 130, the unique access key K in response to receiving the control signal S1.

The randomized numeric code C may be received in the patient application 110 in response to a user, i.e. the patient P, registering/inputting the code using one or more input devices (not shown in the figure) that is/are integrated in, connected to or communicatively coupled to the electronic user device 120. The one or more input devices may e.g. be in the form of a keyboard, touch functionality, speech to text functionality, or any other suitable input device known in the art. According to different embodiments, the randomized numeric code C may, before it is input into the patient application 110, be communicated to the patient P orally by the medical staff/caregiver/host, or sent as a digital signal from the host application 130 to the patient application 110, using any suitable communication protocol and communication method known in the art. As non-limiting examples, the randomized numeric code C could be sent in the form of a short message service (SMS), e-mail, or a message in the patient application interface.

Method step 310 may further comprise, and the host application 130 may further be configured to, setting/configuring the numbers of digits in the randomized numeric code C and/or the length of time of validation of the randomized numeric code C.

In sub-step 320: Storing the second part K_2 of the unique access key K in a memory 160 accessible to the host application 130, wherein the second part K_2 is stored in association with information identifying the patient P.

In sub-step 330: Sending the first part K_1 of the unique access key K from the host application 130 to the patient application 110.

In sub-step 340: Storing the first part K_1 of the unique access key K in a memory 150 accessible to the patient application 110.

In some embodiments, identifying the patient P associated with the received patient data D, based on the second part K_2 of the access key K comprises:
- generating a second part K_2 of the access key K, based on the received first part K_1 of the access key K;
- comparing the generated second part K_2 of the access key K to one or more second parts of access keys stored in the memory 160 accessible to the host application 130 to find a matching second part, wherein the stored one or more second parts of access keys have been generated during pairing of the host application 130 with one or more patient applications 110; and
- if a matching second part of an access key is found, identifying the patient P as the patient associated with the matching second part stored in the memory (160).

A substantial advantage of using a unique access key K that is unrelated to any information identifying the patient P, is that the access key K, or any of its parts K_1 and K_2, cannot by themselves be linked to the patient P. Should the patient data D fall into the hands of someone other than the intended user of the host application or host server, the patient's identity is thereby protected.

In one or more embodiments, the first part K_1 of the unique access key K is the original key and the second part K_2 of the unique access key K is a hash or thumbprint of the original key.

The method may comprise, to generate the second part K_2 of the access key K based on the received first part K_1 of the access key K, running a mathematical function on the first part K_1.

The host application 130 may correspondingly be configured to run a mathematical function on a first part K_1 of a unique access key K to generate a second part K_2 of the unique access key K.

The method according to any of the embodiments presented herein may further comprise, prior to pairing the patient application 110 and the host application 130:
- authenticating a caregiver as an authorized user of the host application 130, using strong authentication; and
- authenticating a patient as an authorized user of the patient application 130, using strong authentication.

Authenticating the caregiver may be performed using the host application 130, e.g. during login.

Authenticating the patient P may be performed using a patient application 110, e.g. during login. Alternatively, authenticating the patient P may be performed by identifying the patient P at the check-in desk in a hospital or the like, by using a driver's license, passport or similar.

The method according to any of the embodiments presented herein may further comprise storing the received patient data D in the memory 150 accessible to the patient application 110.

FIG. 4 shows a flow diagram illustrating a process for secure communication of digital information, comprising steps according to one or more embodiments of the proposed method. The patient in the description of FIG. 4 below corresponds to the patient P.

The process of applying secure communication by transferring information that does not include personal or individual identity information consist of a number of steps.

Below, the process of secure communication illustrated in FIG. 4 is described in more detail:

1. The PC is imported both into the caregiver's host application and into the patient's app. Referring to the reference numbers in FIG. 4, this is step 1.
2. The PC is customized in the host application
   a. Configuring the numbers of digits in the randomized code
   b. Length of time of validation of the randomized code
   Referring to the reference numbers in FIG. 4, this is step 2.
3. In the patient's app it is configured when information should be transferred between the patient app and host application. Referring to the reference numbers in FIG. 4, this is step 3.
4. Identification
   a. The patient is securely identified at the check-in desk in a hospital by using a driver's license or similar identification.
   b. The medical staff is securely identified via login using strong authentication in the host application.
   Referring to the reference numbers in FIG. 4, this is step 4. As can be seen from step 4 in FIG. 4, the identification of the patient can be performed e.g. in the hospital reception. Further applicable options are presented in connection with FIG. 2.
5. The medical staff asks the patient to download the patient app in her smartphone during the physical meeting
6. The medical staff asks the patient to open the patient app in her smartphone during the physical meeting. Referring to the reference numbers in FIG. 4, this is part of step 5. 7. The medical staff generates a randomized set of numbers (i.e. a random code) for the specific patient attending the physical meeting in the host application. The host application generates the randomized set of numbers through the imported PC. Referring to the reference numbers in FIG. 4, this is part of step 6. This corresponds to generating the randomized numeric code C according to embodiments presented herein.
8. The medical staff forwards the given randomized set of numbers orally to the patient during the meeting in person. Referring to the reference numbers in FIG. 4, this is part of step 6.
9. The patient records the randomized set of numbers in the patient's app accessed through/installed in her smartphone during the meeting in person. Referring to the reference numbers in FIG. 4, this is step 7.

The randomized numeric code C may alternatively be communicated directly from the host application 130 and received in the patient application, according to embodiments presented herein.

10. A technical pairing is made between the caregiver's host application and the patient app. Referring to the reference numbers in FIG. 4, this is part of step 8. This corresponds to the pairing described in connection with FIG. 2.
11. Information is hereafter securely and automatically transferred according to the PC configuration between the patient's app and the caregiver's host application every time new relevant data is generated and stored in the patient's app. The message does not include any personal or individual identity information during the transfer of information over the Internet or any other network. Referring to the reference numbers in FIG. 4, this is part of step 8 and step 9.
12. The pairing between the host application and patient app is terminated when either:
    a. The patient deletes the patient app from her smartphone
    b. The healthcare provider deletes the patient in the host application by deleting the hash that is related to the patient. Referring to the reference numbers in FIG. 4, this is step 10.

Login into the patient app, by the patient, may include entering/inputting a password or other data that is unrelated to the patient's identity. This is preferable compared to using e.g. Bank ID or other methods that are linked to the patient's identity, and therefore potentially could be used to identify the patient who is using the patient app and sending her confidential patient data.

How the technical pairing between the caregiver's host application and the patient's app is conducted is described in more detail below:

i. The medical staff requests a randomized set of numbers for the identified patient in front of her in the host application.

ii. An ID is created in the host application for this specific patient. This ID is not based on a personal ID and cannot be linked to an individual's identity.

iii. When the randomized set of numbers, that has been given orally to the patient, is registered in the patient's app, the PC in the patient's app sends a message to the PC in the host application.

iv. When the host application receives the message the PC in the host application generates an access key that is sent to the patient app;
   a. The access key is made up of two parts: a) an original key that the patient app holds and b) a hash of the original key that the host application holds.
   b. The PC in the host application run a mathematical function on the access key when received from the patient app. The mathematical function generates the hash of the original key.

This access key corresponds to the unique access key K, having the two parts K_1 and K_2, according to embodiments presented herein.

v. A hash/thumbprint of the access key that has been is stored in the host application; (it is a hash/thumbprint of the access key sent to the patient app)

vi. Every time the patient's app transfer data to the host application the access key is accompanied/sent together with this transfer vii. When the host application receives the message from the patient app the received accompanied access key is run through a mathematic function. The outcome from running the access key through mathematical function is this patient's hash.

viii. This hash/thumbnails is compared with the hashes stored in the host application to look up a match and the identification of the patient that has sent the data. This is an embodiment of how to identify the patient P associated with the received patient data D, based on the second part K_2 of the access key K, as described herein.

The patient connector is configured with anything from 1 to an infinite number of digits. Recommended is to provide with a random code consisting of at least 8 digits. To perform the pairing, the code is given by word of mouth from for instance a medical professional working in the host application to a patient.

The patient must to pair enter the numeric code into her client application in her smartphone. Alternatively, the numeric code is communicated directly from the host application 130 to the patient application according to any of the embodiments presented herein. The app client must call the host server code within a certain time, otherwise the code is invalid. The duration is set to 30 minutes, or any other suitable duration depending on circumstances.

The code is checked and if it is valid it is paired to the identity of a patient on the application and an access key is generated. This access key is returned to the patient app. A hash of the access key is stored on the host application; it is used to derive which patient it is that has communicated data from a patient app to the host application. The solution has thus achieved a connection between a patient app and a caregiver's host application. The access key itself does not contain any information about to whom the information sent belongs. Future connections between the patient's app and the caregiver's host application will use the same access key every time a transfer is made, enabling the host application to always know from which patient the data is sent.

The secure communication will advantageously be exercised in a computerized system and/or through the internet or any other network.

The PC will advantageously be utilized within any work in society that can benefit from continuous access to secure and accurate individual registered data.

In one or more embodiments, the patient application 110 and/or the host application 130 may be configured to perform any or all of the relevant method steps and functions presented herein.

Figure 3:
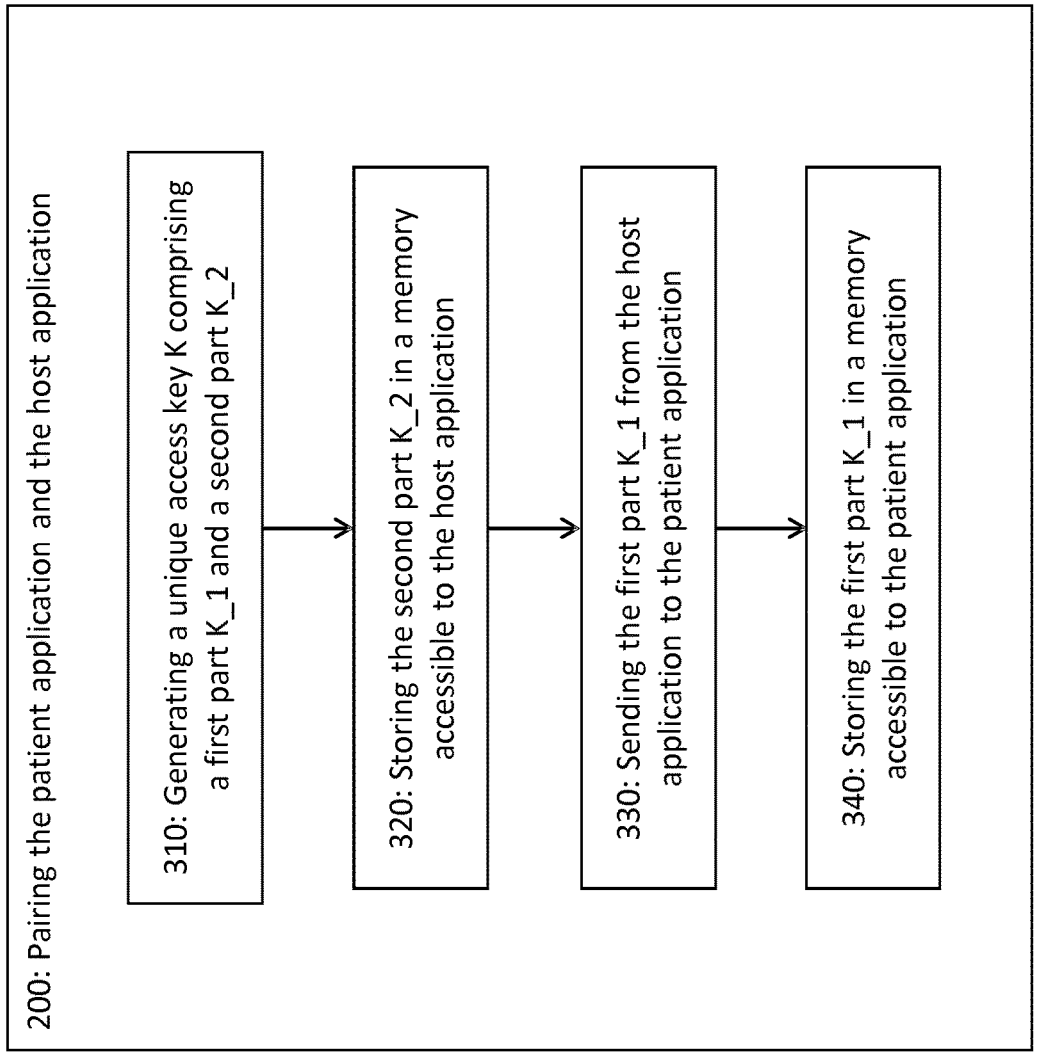
FIG. 3 shows a flow diagram illustrating one or more embodiments of the proposed method.

All of the process steps, as well as any sub-sequence of steps, described with reference to FIG. 2, 3 or 4 above may be controlled by means of a programmed processor. Moreover, although the embodiments of the invention described above with reference to the drawings comprise processor and processes performed in at least one processor, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Video/Versatile Disk), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

In some embodiments, there is provided a computer program loadable into a non-volatile data carrier communicatively connected to a processing unit, the computer program comprising software for executing the method according any of the method embodiments presented herein when the program is run on the processing unit. In some embodiments, there is provided a non-volatile data carrier containing the computer program.

The term "comprises/comprising" when used in this specification is taken to specify the presence of stated features, integers, steps or components. However, the term does not preclude the presence or addition of one or more additional features, integers, steps or components or groups thereof.

The invention is not restricted to the described embodiments in the figures, but may be varied freely within the scope of the claims.

The invention claimed is:

1. A method in a healthcare monitoring system for anonymous communication of patient data associated with a patient from an electronic user device, using a patient application implemented in the electronic user device, to a host server, using a host application implemented in the host server, via a wireless network, and identification of the patient associated with the patient data after the patient data is received in the host server comprising:
   pairing the patient application and the host application, wherein the pairing comprises:
   i) generating a unique access key for the patient, using the host application wherein the unique access key comprises a first part and a second part, wherein the first part of the unique access key is the original key and the second part of the unique access key is a hash or thumbprint of the original key, and wherein the unique access key, or any of its parts, cannot by themselves be linked to the patient;
   ii) storing the second part of the unique access key in a memory accessible by the host application, wherein the second part is stored in association with information identifying the patient;
   iii) sending the first part of the unique access key from the host application to the patient application;
   iv) storing the first part of the unique access key in a memory accessible by the patient application;
   receiving in the patient application patient data, from at least one patient data registering device;
   in response to receiving patient data in the patient application, sending the received patient data and the first part of the access key to the host application, wherein the patient data does not comprise any information identifying the patient;
   receiving in the host application the patient data and the first part of the access key; and identifying the patient associated with the received patient data, based on the second part of the access key by:
  i) generating a second part of the access key, based on the received first part of the access key;
  ii) comparing the generated second part of the access key to one or more second parts of access keys stored in the memory accessible to the host application to find a matching second part, wherein the stored one or more second parts of access keys have been generated during pairing of the host application with one or more patient applications; and
  iii) if a matching second part of an access key is found, identifying the patient as the patient associated with the matching second part stored in the memory.

2. The method of claim 1, wherein the method further comprises, prior to pairing the patient application and the host application:
authenticating a caregiver as an authorized user of the host application, using strong authentication; and
authenticating a patient as an authorized user of the patient application, using strong authentication.

3. The method of claim 2, wherein authenticating the caregiver is performed using the host application.

4. The method of claim 2, wherein authenticating the patient is performed using the patient application.

5. The method of claim 1, further comprising storing the received patient data in the memory accessible to the patient application.

6. The method of claim 1, wherein generating a unique access key for the patient comprises:
generating, using the host application, a randomized numeric code that is unrelated to any information identifying the patient;
receiving, in the patient application, the randomized numeric code;
sending a message in the form of a control signal from the patient application to the host application in response to receiving the unique access key;
receiving, in the host application, the control signal; and
generating, in the host application, the unique access key in response to receiving the control signal.

7. A healthcare monitoring system for anonymous communication of patient data associated with a patient from an electronic user device to a host server, via a wireless network, and identification of the patient associated with the patient data after the patient data is received in the host server, wherein:
the electronic user device comprises a patient application;
the host server comprises a host application;
the patient application is configured to communicate with the host application via the wireless network;
the system further comprises a memory accessible by the patient application, and a memory accessible by the host application;
wherein the system is configured to pair the patient application and the host application, by:
the host application being configured to:
i) generate a unique access key for the patient, wherein the unique access key comprises a first part and a second part, wherein the first part of the unique access key is the original key and the second part of the unique access key is a hash or thumbprint of the original key, and wherein the unique access key, or any of its parts, cannot by themselves be linked to the patient;
ii) store the second part of the unique access key in the memory accessible by the host application, wherein the second part is stored in association with information identifying the patient; and
iii) send the first part of the unique access key to the patient application;
the patient application being configured to:
i) receive the first part of the unique access key from the host application;
ii) store the received first part of the unique access key in the memory accessible by the patient application;
iii) receive patient data, from at least one patient data registering device; and
iv) in response to receiving patient data in the patient application, send the received patient data and the first part of the access key to the host application, wherein the patient data does not comprise any information identifying the patient; and
the host application further being configured to:
i) receive patient data and the first part of the access key from the patient application; and
ii) identify the patient associated with the received patient data, based on the received second part of the access key, by:
generating a second part of the access key, based on the received first part of the access key;
comparing the generated second part of the access key to one or more second parts of access keys stored in the memory accessible to the host application to find a matching second part, wherein the stored one or more second parts of access keys have been generated during pairing of the host application with one or more patient applications; and
if a matching second part of an access key is found, identifying the patient as the patient associated with the matching second part stored in the memory.

8. The healthcare monitoring system of claim 7, wherein the host application is configured to authenticate a caregiver as an authorized user of the host application, using strong authentication, prior to the pairing of the patient application and the host application.

9. The healthcare monitoring system of claim 7, wherein the patient application is configured to authenticate a patient as an authorized user of the patient application, using strong authentication, prior to the pairing of the patient application and the host application.

10. The healthcare monitoring system of claim 7, wherein, in order to generate a unique access key for the patient:
the host application is configured to generate a randomized numeric code that is unrelated to any information identifying the patient;
the patient application is configured to receive the randomized numeric code from the host application; and send a message in the form of a control signal to the host application in response to receiving the unique access key; and
the host application is configured to receive the control signal from the patient application; and generate the unique access key in response to receiving the control signal.

11. A computer program loadable into a non-volatile data carrier communicatively connected to a processing unit, the computer program comprising software for executing the method according claim 1 when the program is run on the processing unit.

12. A non-volatile data carrier containing the computer program of claim 11.

\* \* \* \* \*